United States Patent [19]

Lee et al.

[11] Patent Number: 5,049,696

[45] Date of Patent: Sep. 17, 1991

[54] ANTIHYPERCHOLESTEROLEMIC COMPOUNDS

[75] Inventors: Ta J. Lee, Lansdale; Clarence S. Rooney, Worcester; William F. Hoffman, Lansdale, all of Pa.

[73] Assignee: Merck & Co., Inc., Rahway, N.J.

[21] Appl. No.: 366,085

[22] Filed: Jun. 14, 1989

Related U.S. Application Data

[62] Division of Ser. No. 177,806, Apr. 11, 1988, Pat. No. 4,847,306.

[51] Int. Cl.$^5$ .................... C07C 69/76; C07C 69/74; A01N 43/16
[52] U.S. Cl. ........................................ 560/75; 560/85; 560/117; 560/119; 560/125; 560/126
[58] Field of Search ................ 560/55, 75, 117, 119, 560/125, 126; 514/532, 533, 824

[56] References Cited

U.S. PATENT DOCUMENTS 4,376,863  3/1983  Lam .
4,450,171  5/1984  Hoffman et al. .................. 424/279

FOREIGN PATENT DOCUMENTS 211416  2/1987  European Pat. Off. .
251625  1/1988  European Pat. Off. .
327165  8/1989  European Pat. Off. .
090509  5/1983  Japan .
048418  3/1984  Japan .
303952  12/1988  Japan .

*Primary Examiner*—Paul J. Killos
*Attorney, Agent, or Firm*—Melvin Winokur; Joseph F. DiPrima

[57] ABSTRACT

Novel 3-hydroxy-3-methylglutaryl-Coenzyme A(HMG-CoA) reductase inhibitors, which are useful as antihypercholesterolemic agents and are represented by the following general structural formulae (I) and (II)

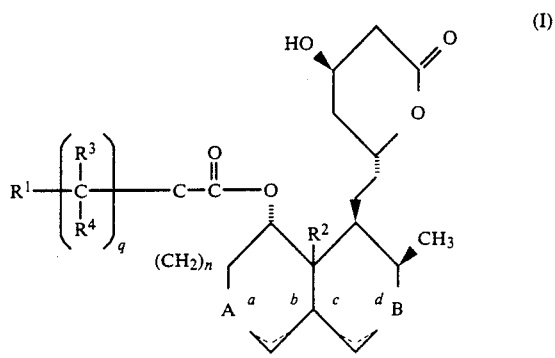

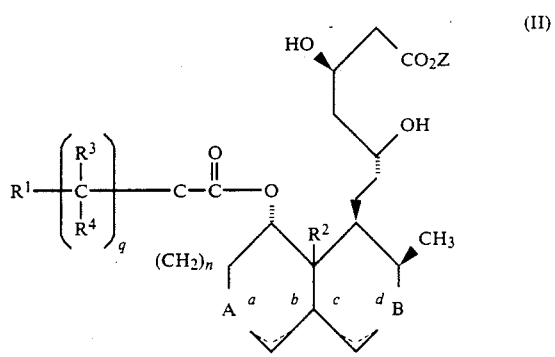

and pharmaceutically acceptable salts of the compound (II) in which Z is hydrogen are disclosed.

23 Claims, No Drawings

ANTIHYPERCHOLESTEROLEMIC COMPOUNDS

This is a division of application Ser. No. 177,806 filed Apr. 11, 1988 now U.S. Pat. No. 4,847,306 issued July 11, 1989.

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occurring compounds and their semi-synthetic analogs have the following general structural formulae:

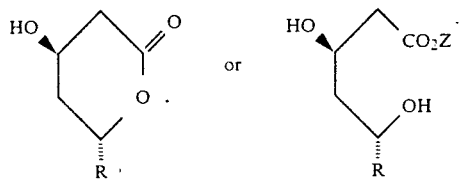

wherein:
Z is hydrogen, $C_{1-5}$ alkyl or $C_{1-5}$ alkyl substituted with a member of the group consisting of phenyl, dimethylamino, or acetylamino;
R is

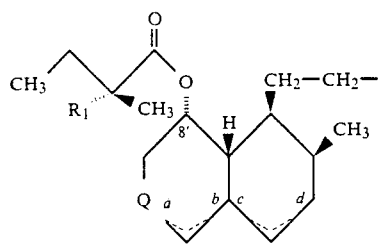

wherein
Q is

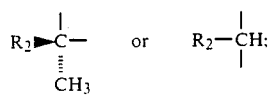

$R_2$ is H or OH;
$R_1$ is hydrogen or methyl; and a, b, c, and d represent optional double bonds, especially where b and d represent double bonds or a, b, c, and d are all single bonds.

U.S. Pat. No. 4,517,373 discloses semi-synthetic compounds represented by the above general formula wherein R is

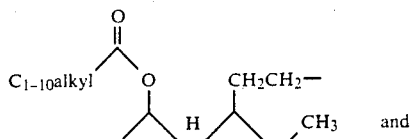

U.S. Pat. No. 4,346,227 and U.S. Pat. No. 4,448,979 also disclose semi-synthetic compounds represented by the above general formula wherein R is

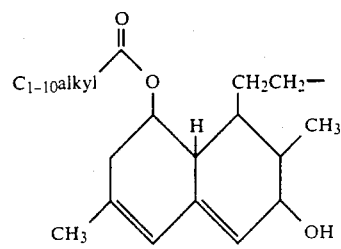

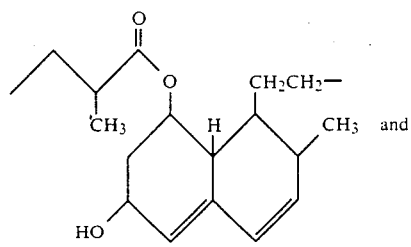

Japanese unexamined patent application J59-122,483-A discloses a semi-synthetic compound represented by the above general formula wherein R is

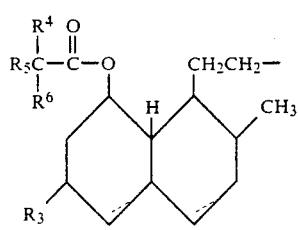

in which
$R_3$ is hydrogen or methyl;
$R_4$ is hydrogen, halogen or haloalkyl;
$R_5$ is hydrogen, halogen or loweralkyl
and $R_6$ is halogen, $N_3$, hydroxy, thio, amino, loweralkoxy, loweralkylthio and aralkylthio.

U.S. Pat. No. 4,444,784 discloses 8'-acyloxy derivatives of compactin, mevinolin and the dihydro and tetrahydro analogs thereof. Generically disclosed are the compounds represented by the above general formula wherein R is

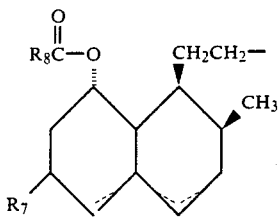

in which $R_7$ is hydrogen or methyl and $R_8$ is $C_{3-10}$ cycloalkyl.

SUMMARY OF THE INVENTION

This invention relates to novel compounds which are HMG-CoA reductase inhibitors and are useful as antihypercholesterolemic agents. Specifically, the compounds of this invention are semi-synthetic analogs of compactin, mevinolin, hydroxylated compactin and hydroxylated mevinolin and the dihydro and tetrahydro analogs thereof which possess a specifically substituted cycloalkyl 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

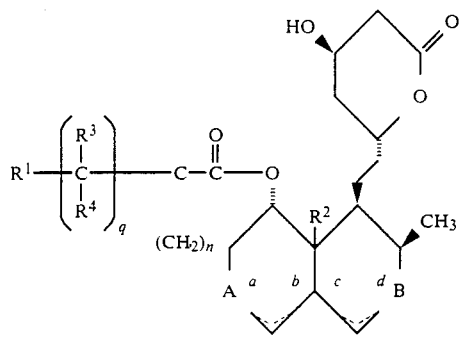

(I)

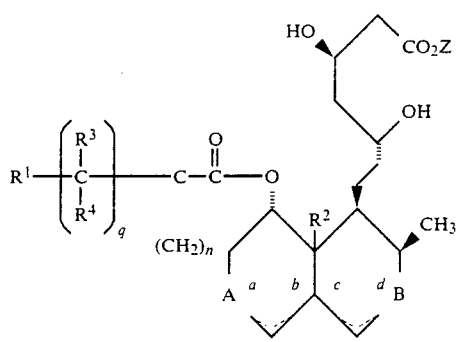

(II)

wherein:
q is 0 to 5;
n is 2 to 7;

$R^1$ is $C_{1-6}$ alkyl, $C_{1-6}$ alkyl substituted with a group selected from halogen, hydroxy, $C_{1-3}$ alkylthio, $C_{1-3}$ alkylsulfinyl and $C_{1-3}$ alkylsulfonyl, $C_{1-6}$ alkylthio, $C_{1-6}$ alkylsulfinyl, $C_{1-6}$ alkylsulfonyl, $C_{3-7}$ cycloalkylthio, $C_{3-7}$ cycloalkylsulfinyl, $C_{3-7}$ cycloalkylsulfonyl, $C_{3-7}$ cycloalkyl, phenyl, or phenyl substituted with X and Y;

$R^2$ is hydrogen or hydroxy;

$R^3$ and $R^4$ independently are hydrogen, $C_{1-3}$ alkyl, $C_{3-7}$ Cycloalkyl, phenyl or phenyl substituted with X and Y and when q is 2 to 5, each of the $R^3$s and $R^4$s are independently hydrogen, $C_{1-3}$ alkyl, $C3-7$ cycloalkyl or only one of the $R^3$s and $R^4$s is phenyl or substituted phenyl;

A is

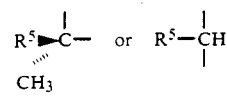

in which $R^5$ is hydrogen or hydroxy;

B is $CHR^6$ in which $R^6$ is hydrogen or hydroxy;

a, b, c and d represent single bonds, one of a, b, c or d represents a double bond or both a and c or both b and d represent double bonds, provided that when a is a double bond, A is

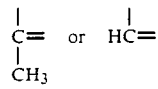

and when d is a double bond,
B is

X and Y independently are hydrogen, halogen, trifluoromethyl, $C_{1-3}$ alkyl, nitro, cyano or a group selected from;

a) $R^7O(CH_2)_m$ in which m is 0 to 3 and $R^7$ is hydrogen, $C_{1-3}$ alkyl or hydroxy-$C_{1-3}$ alkyl;

b)

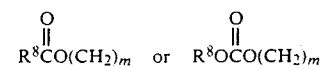

in which $R^8$ is hydrogen, $C_{1-3}$ alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl;

c)

in which $R^9$ is hydrogen, $C_{1-3}$ alkyl, hydroxy-$C_{1-3}$ alkyl, $C_{1-3}$ alkoxy-$C_{1-3}$ alkyl, phenyl or naphthyl;

d) $R^{10}R^{11}N(CH_2)_m$,

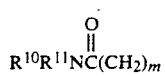

or

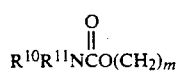

in which $R^{10}$ and $R^{11}$ independent are hydrogen, $C_{1-3}$ alkyl, hydroxy-$C_{2-3}$ alkyl or together with the nitrogen atom to which they are attached form a heterocycle group selected from piperidinyl, pyrrolidinyl, piperazinyl, morpholinyl or thiomorpholinyl;

e) $R^{12}S(O)_p(CH_2)_m$ in which p is 0 to 2 and $R^{12}$ is hydrogen, $C_{1-3}$ alkyl, amino, $C_{1-3}$ alkylamino or di alkyl)amino;

Z is hydrogen, $C_{1-5}$ alkyl or $C_{1-5}$ alkyl substituted with a group selected from phenyl, dimethylamino or acetylamino; and pharmaceutically acceptable salts of the compounds of the formula (II) in which Z is hydrogen.

One embodiment of this invention is the class of compounds of the formula (I) and (II) wherein q is 0, $R^2$, $R^5$ and $R^6$ are hydrogen and a, b, c and d represent single bonds or both b and d represent double bonds. Particular compounds of this embodiment are those of the formulae (I) and (II) wherein n is 2 to 5 and $R^1$ is $C_{1-6}$ alkyl, hydroxy-$C_{1-6}$ alkyl, $C_{1-6}$ alkylthio, phenyl or hydroxyphenyl.

Illustrative of this embodiment when n is 2 is the following compound:

6(R)-[2-[8(S)-(1-Methylcyclopropanecarbonyloxy)-2(S),6(R)-dimethyl1,2,6,7,8,8a(R)-hexahydronaphthyl-1(S)]ethyl]-4(R)-hydroxy-3,4,5,6-tetrahydro-2H-pyran-2-one.

Illustrative of this embodiment when n is 3 are the following compounds:

(1) 6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-[1-(3-Hydroxypropyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-[1-[(4-Hydroxyphenyl)methyl]cyclobutanecarbonyloxy]-2(S),6(R)dimethyl-1,2,6,7,8,8a(R)-hexahydronaphthyl-1(S)]ethyl]-4(R)-hydroxy-3,4,5,6-tetrahydro-2H-pyran-2-one;

(5) 6(R)-[2-[8(S)-[1-(1-Hydroxymethyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and (6) 6(R)-[2-[8(S)-[(1-Phenylmethyl)cyclobutanecarbonyloxy)]-2(S),6(R)-dimethyl-1,2,6,7,7,8a(R)-hexahydronaphthyl-1(S)]ethyl]-4(R)-hydroxy-3,4,5,6-tetrahydro-2H-pyran-2-one.

Illustrative of this embodiment when n is 4 are the following compounds:

(1) 6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and (2) 6(R)-[2-[8(S)-(1-Methylthiocyclopentanecarbonyl)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

Illustrative of this embodiment when n is 5 is the following compound:

6(R)-[2-[8(S)-(1-Methylcyclohexanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

Another embodiment of this invention is the class of compounds of the formula (II) wherein Z is hydrogen or $C_{1-5}$ alkyl and pharmaceutically acceptable salts of the compounds of the formula (II) wherein Z is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of formula (I) are conveniently prepared from compactin, mevinolin, or the appropriate dihydro or tetrahydro analog thereof via the following general synthetic pathways:

Pathway A:

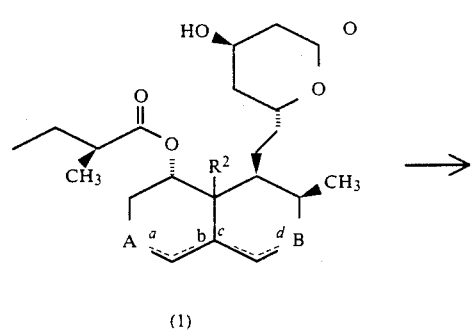

(1)

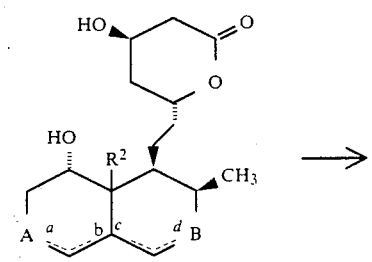

(2)

-continued
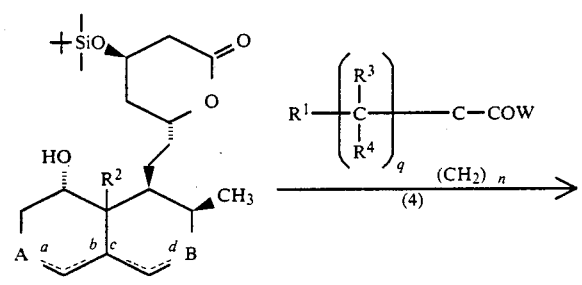
(3)
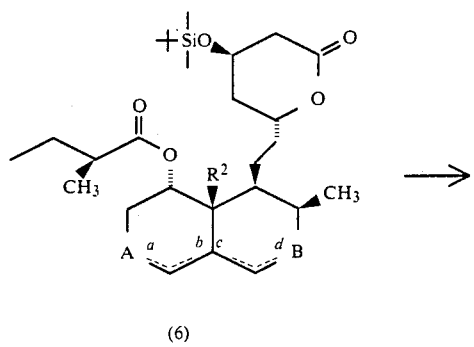
(6)
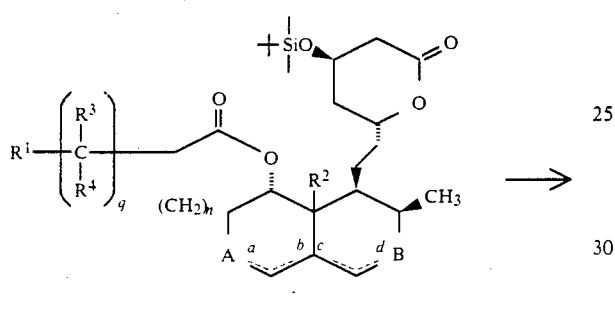
(5)
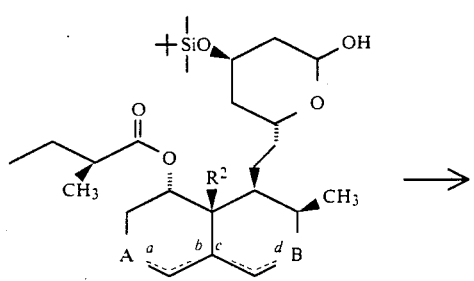
(7)
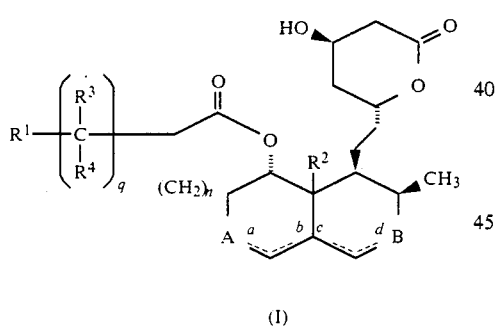
(I)
Pathway B
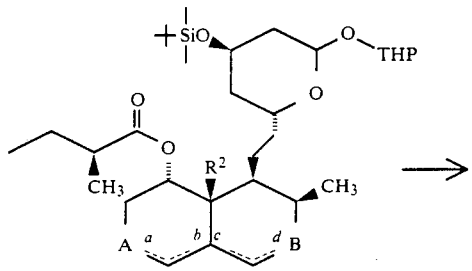
(8)
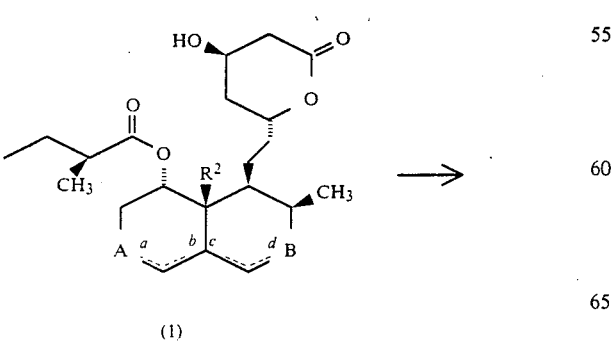
(1)
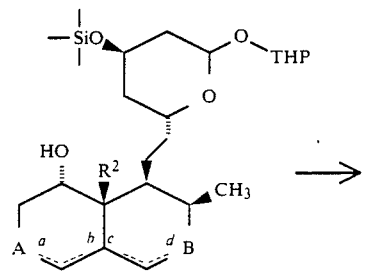
(9)

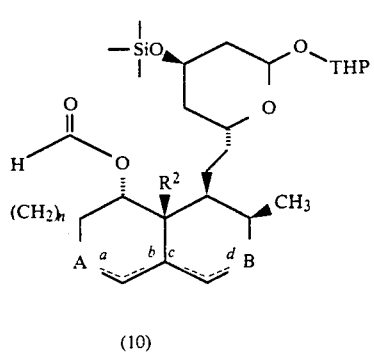

(10)

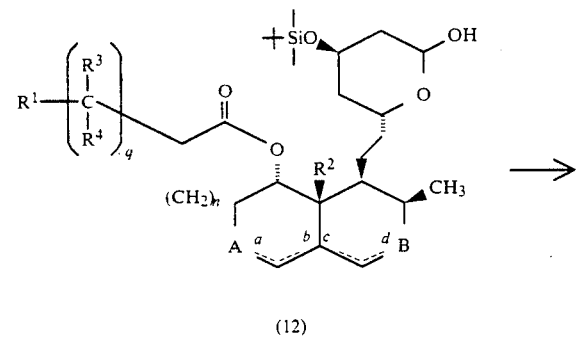

(11)

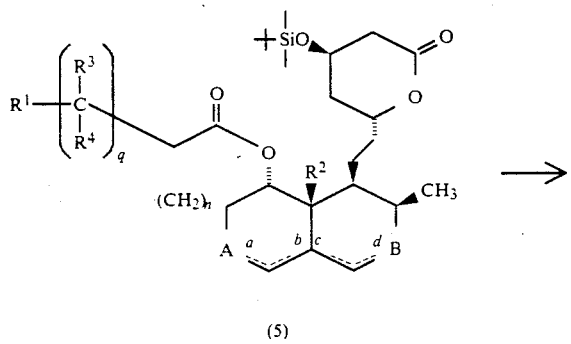

(12)

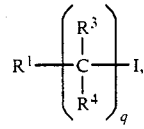

(5)

-continued

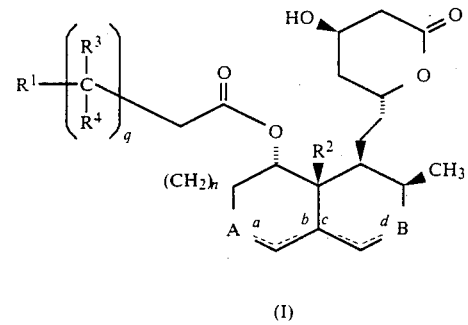

(I)

The starting materials compactin, mevinolin, and their dihydro and tetrahydro analogs are readily available or may be prepared according to fermentation procedures disclosed in U.S. Pat. No. 3,983,140, U.S. Pat. No. 4,049,495, U.S. Pat. No. 4,231,938, U.S. Pat. No. 4,294,846, U.S. Pat. No. 4,343,814 and the hydrogenation procedures disclosed in U.S. Pat. No. 4,351,844.

According to Pathway A, the appropriate starting material of formula (1) is hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784 to give the compounds of the formula (3).

Acylation of the 8'-hydroxy group of the compounds of the formula (3) is accomplished under suitable conditions using the reagents of formula (4) wherein q, n, $R^1$, $R^3$ and $R^4$ are described above and W is hydroxy or halogen, especially chloro or bromo. The protecting groups of the resultant compounds of the formula (5) are removed utilizing suitable conditions to afford the compounds of the formula (I).

According to Pathway B, the 2-carbonyl function in the lactone moiety of the compounds of formula (6) is reduced to the lactol function under standard conditions to yield the compounds of the formula (7). The 2-hydroxy function in the lactol moiety of the compounds of the formula (7) is then protected with a suitable protecting group, exemplified here as the tetrahydropyran group (THP). The compounds of the formula (8) are converted to the compounds of the formula (9). The compounds of the formula (9) so produced are reacted with an acylating agent of the formula $$H-C-COW$$
$$|$$
$$(CH_2)_n$$

wherein n and W are defined above to afford the compounds of the formula (10). The enolates of the compounds of the formula (10) are then reacted with the appropriately alkylating agent, $$R^1 \!\!-\!\!\left(\!\!\begin{array}{c} R^3 \\ | \\ C \\ | \\ R^4 \end{array}\!\!\right)_{\!\!q}\!\!-\!\!I,$$

wherein q, $R^1$, $R^3$ and $R^4$ are described above, to give the compounds of formula (11). The THP protecting group is removed under acidic conditions and the resulting hydroxy function is oxidized to form the 2-carbonyl function of the lactone moiety of the compounds of the formula (5). The remaining protecting groups on the compounds of the formula (5) are removed under standard conditions to yield the compounds of the formula (I).

For the compounds of this invention wherein the polyhydronaphthyl moiety is substituted with a hydroxy group, the compounds of the formula (4) are subject to a microbiological hydroxylation after the removal of the protecting groups utilizing the general procedures disclosed in U.S. Pat. No. 4,346,227, U.S. Pat. No. 4,448,979, U.S. Pat. No. 4,517,373 and Japanese Pat. No. Application J-60-130,548.

The compounds of the formula (II) wherein Z is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 2 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in J. Med. Chem., 28, P. 347–358 (1985) and described below:

Isolation of HMG-CoA Reductase

Male Holtzman Sprague-Dawley rate (225–250g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsome by the method of Heller and Shrewsbury [J. Biol. Chem., 1976, 251,3815], and purified through the second ammonium sulfate precipitation step as described by Kleinsek et al. [Proc. Natl. Acad. Sci. USA, 1977, 74, 1431]. The enzyme preparation was tested for HMG-CoA reductase potency and diluted with 100 mM phosphate buffer (pH 7.2) so that 100 μL of the enzyme solution, when added to the assay control, gave a value of 50,000–60,000 dpm. The enzyme preparation was stored at −80° C.

HMG-CoA Reductase Inhibition Assay

The assay is essentially the procedure of Shefer et al., [J. Lipid Res., 1972, 13, 402]. The complete assay medium contained the following in a total volume of 0.8 mL: phosphate buffer, pH 7.2, 100 mM; $MgCl_2$, 3 mM; NADP, 3 mM; glucose 6-phosphate, 10 mM; glucose-6-phosphate dehydrogenase, 3 enzyme units; reduced glutathione, 50 mM; HMG-CoA (glutaryl-3- $^{14}C$, New England Nuclear), 0.2 mM (0.1 μCi); and partially purified enzyme stock solution, 100 μL.

Test compounds or compactin (after first being converted to the sodium salt of their dihydroxy acid form in situ by addition of 1 N NaOH (1 equiv)) were added to the assay system in 10-μL volumes at multiconcentration levels. After a 40-minute incubation at 37° C. with shaking and exposure to air, the reaction was stopped by the addition of 0.4 mL of 8 N HCl. After an additional 30-minute incubation period at 37° C. to ensure the complete lactonization of mevalonic acid to mevalonolactone, 0.2 mL of the mixture was added to an 0.5×5.0 cm column containing 100–200-mesh Bio-Rex 5, chloride form (Bio-Rad), wetted with distilled water, as described by Alberts et al. [J. Proc. Natl. Acad. Sci. U.S.A., 1980, 77, 3957]. The unreacted [$^{14}C$]HMG-CoA was absorbed on the resin and the [$^{14}C$]mevalonolactone was eluted with distilled water (2×1 mL) directly into 7-mL scintillation vials. Five milliliters of Aquasol-2 (New England Nuclear) was added to each vial, and radioactivity was measured in a Packard Tri Carb Prias scintillation counter. $IC_{50}$ values were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG-CoA reductase inhibitory activities of the claimed compounds tabulated for a number of the claimed compounds are the relative potencies for said compound.

TABLE 1

| T | Relative Potency[1] |
|---|---|
| $CH_3-C\underset{CH_2-CH_2}{\overset{}{\diagup\!\!\!\diagdown}}$ | 76 |

TABLE 1-continued

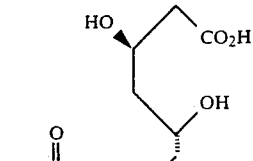

| T | Relative Potency[1] |
|---|---|
| 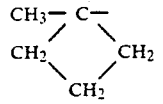 | 171 |
| 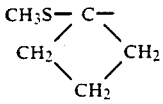 | 240 |
| 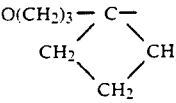 | 100 |
| 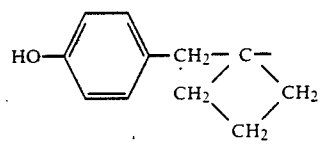 | 200 |
| 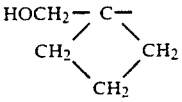 | 88 |
| 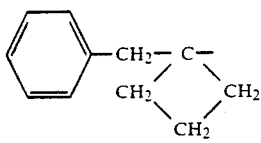 | 156 |
| 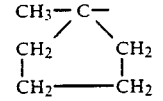 | 188 |
| 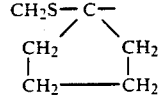 | 167 |
| 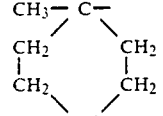 | 217 |

Included within the scope of this invention is the method of treating arteriosclerosis, familial hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(1-Methylcyclopropanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one]

(a)
6(R)-[2-[8(S)-(1-Methylcyclopropanecarbonyloxy)-2(S),6(R)-dimethyl-1,2,6,7,8,8a(R)hexahydronaphthyl-1(S)]ethyl]-4(R)-(dimethyl-tert-butylsilyloxy)3,4,5,6-tetrahydro-2H-pyran-2-one (1a)

To a stirred solution of 6(R)-[2-[8(S)hydroxy-2(S),6(R)-dimethyl-1,2,6,7,8,8a(R)-hexahydronaphthyl-1(S)]ethyl-4(R)-(dimethyl-tert-butylsilyloxy)-3,4,5,6-tetrahydro-2H-pyran-2-one (1.0 g, 2.3 mmol) and 4-dimethylaminopyridine (0.17 g, 1.38 mmol) in pyridine (15 ml) was added under nitrogen 1-methylcyclopropanecarbonyl chloride (0.82 g, 6.9 mmol). The resulting mixture was stirred at room temperature for 1 hour, then heated at 60° C. for 8 hours. More 4-dimethylaminopyridine (30 mg) and 1-methylcyclopropanecarbonyl chloride (0.27 g) were added and the resulting mixture was heated at 60° C. for 8 hours. The reaction mixture was poured into cold water and extracted with ether. The ethereal extract was washed successively with 1N HCl, 5% NaHCO$_3$ and brine. It was dried over MgSO$_4$, filtered and evaporated to leave an oily residue which was purified by flash chromatography on a silica gel column. Elution of the column with CH$_2$Cl$_2$:acetone=200:1 (v:v) gave the desired product as a pale yellow oil: NMR (CDCl$_3$)δ 0.09 (6H, s), 0.89 (9H, s), 1.07 (3H, d, J=7 Hz), 1.25 (3H, s), 2.57 (2H, d, J=4 Hz), 4.30 (1H, m), 4.60 (1H, m), 5.27 (1H, m), 5.50 (1H, m), 5.74 (1H, dd, J=10 Hz, 5 Hz), 5.98 (1H, d, J=10 Hz).

(b)
6(R)-[2-[8(S)-(1-Methylcyclopropanecarbonyloxy)-2(S),6(R)-dimethyl-1,2,6,7,8,8a(R)-hexahydronaphthyl-1(S)]ethyl]-4(R)-hydroxy3,4,5,6-tetrahydro-2H-pyran-2-one A solution of tetra-n-butylammonium fluoride solution (1M in THF, 12 ml, 12 mmo)) was added to a stirred solution of the Compound 1(a) (0.7 g, 1.35 mmol) and acetic acid (1.45 ml, 25 mmol) in THF (75 ml). The resulting mixture was stirred under nitrogen for 20 hours. The reaction mixture was poured into cold water and extracted with ether. This extract was washed with 5% NaHCO$_3$ and brine, dried, filtered and concentrated to give a residue. This residue was purified by flash chromatography. Elution of the column with CH$_2$Cl$_2$:acetone 10:1 (v:v) afforded the desired products which crystallizes after the trituration with hexane:2-propanol=9:1 (v:v). The solid product was collected by filtration and recrystallized from ether/ethyl acetate/hexane: m.p. 181-2° C.; NMR (CDCl$_3$)δ 0.65 (2H, m), 0.90 (3H, d, J=7 Hz), 1.17 (3H, d, J=7 Hz), 1.26 (3H, s), 2.63 (1H, m of d, J=18 Hz), 2.75 (1H, d of d, J=18 Hz, 5 Hz), 4.39 (1H, m), 4.64 (1H, m), 5.28 (1H, m), 5.52 (1H, m), 5.77 (1H, d of d, J=10, 5 Hz), 5.98 (1H, d, J=10 Hz).

Anal. Calcd. for $C_{24}H_{34}O_5$: C, 71.61; H, 8.51. Found: C, 71.69; H, 8.52.

EXAMPLE 2

Preparation of 6(R)-[2-[8(S)-(1-Methylcyclohexanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a)

6(R)-[2-[8(S)-(1-Methylcyclohexanecarbonyloxy)-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (2a)

A solution of 2,6-dichloro-4-methoxy-1,3,5-triazine (0.41 g, 2.3 mmol) in methylene chloride (10 ml) was added dropwise to a stirred solution of 1-methylcyclohexanecarboxylic acid (0.33 g, 2.3 mmol) and N-methylmorpholine (0.260 ml, 2.6 mmol) in methylene chloride (12 ml). The resulting mixture was stirred at $-5°$ C. for 2 hours before a solution of 6(R)-[2-[8(S)-hydroxy-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (0.50 g, 1.1 mmol) in methylene chloride (10 ml) was added. The resulting mixture was heated at reflux for 20 hours, cooled, diluted with ether (100 ml), then washed successively with water, 1N HCl, brine, 5% NaHCO$_3$ and brine. It is dried over magnesium sulfate, filtered and evaporated to yield a residue which was applied to a silica gel column. The column was eluted with CH$_2$Cl$_2$:acetone=200:1 (v:v). Fractions containing the pure Product were combined and evaporated to afford the title compound as a pale yellow oil: NMR (CDCl$_3$) δ=0.09 (6H, s), 0.91 (9H, s), 1.21 (3H, d, J=7 Hz), 1.27 (3H, s), 2.60 (2H, d, J=4 Hz), 4.30 (1H, m), 4 61 (1H, m), 5.3-5.6 (2H, m), 5.75 (1H, d of d, J=10, 5 Hz), 6.01 (1H, d, J=10 Hz).

(b)

6(R)-[2-[8(S)-(1-Methylcyclohexanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Utilizing the general procedure of Example 1(b), the compound (2a) was converted into the desired product as a viscous oil; NMR (CDCl$_3$) δ=0.90 (3H, d, J=7 Hz), 1.11 (3H, d, J=7 Hz), 1.17 (3H, s), 4.40 (1H, m), 4.65 (1H, m), 5.45 (1H, m), 5.52 (1H, m), 5.80 (1H, d of d, J=10 Hz, 5 Hz), 6.02 (1H, d, J=10 Hz).

EXAMPLE 3

Preparation of 6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a)

6(R)-[2-(8(S)-Cyclobutanecarbonyloxy-2(S),6(R)-dimethyl-1,2,6,7,8,8a(R)-hexahydronaphthyl-1(S))ethyl]-4(R)-(tert-butyldimethylsilyloxy)-2-(2-tetrahydropyranyloxy)-3,4,5,6-tetrahydro-2H-pyran (3a)

Cyclobutanecarbonyl chloride (1.37 g, 11.6 mmol) was added under nitrogen to a stirred solution of 6(R)-[2-(8(S)-hydroxy-2(S),6(R)-dimethyl1,2,6,7,8,8a(R)-hexahydronaphthyl-1(S))ethyl]-4(R)(tert-butyldimethylsilyloxy)-2-(2-tetrahydropyranyloxy)-3,4,5,6-tetrahydro-2H-pyran (2 g, 3.84 mmol) and 4-dimethylaminopyridine (0.28 g, 2.28 mmol) in pyridine (28 ml) with the cooling of a cold water bath. The resulting mixture was stirred at room temperature for 12 hours. The reaction mixture was then poured into water and extracted with ether. The extract was successively washed with diluted HCl (to remove pyridine) and aqueous NaHCO$_3$ After the drying and filtration, the filtrate was concentrated to give a residue which was subsequently purified by flash column chromatography. Elution of the column with CH$_2$Cl$_2$:acetone=200:1 (v:v) afforded the desired product as a pale yellow oil NMR (CDCl$_3$) δ=0.06 (6H, s), 0.92 (9H, s), 1.07 (3H, d, J=7 Hz), 3.06 (1H, q, J=8 Hz), 4.26 (1H, m), 4.8-5.2 (2H, m), 5.33 (1H, m), 5.50 (1H, m), 5.75 (1H, d of d, J=10, 5 Hz), 6.00 (1H, d, J=10 Hz).

(b)

6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-(tert-butyldimethylsilyloxy)-2-(2-tetrahydropyranyloxy)-3,4,5,6-tetrahydro-2H-pyran (3b)

To a stirred solution of diisopropylamine (112 μl, 0.8 mmol) and hexamethylphosphoramide (0.173 ml, 1 mmol) in tetrahydrofuran (2 ml) under nitrogen at 0° C. was add n-butyllithium (0.34 ml, 2.36M in hexane, 0.8 mmol). The resulting mixture was stirred at $-78°$ C. for 10 minutes and then a solution of the compound (3a) (0.32 g, 0.53 mmol) in tetrahydrofuran (3 ml) was added dropwise. The reaction mixture was stirred at $-78°$ C. for 30 minutes, then at 0° C. for 30 minutes followed by the addition of methyl iodide (62 μl1.0 mmol) via a syringe. The resulting mixture is stirred at 0° C. for 10 minutes and warmed to ambient temperature over 2 hours. The reaction mixture was then poured into cold water and extracted with diethyl ether. The extracts were washed with water (2×), dried over magnesium sulfate and concentrated in vacuo to give an oily residue. The residue was chromatographed over silica gel eluted with CH$_2$Cl$_2$:acetone=200:1 (v:v) to a afford the desired product as a colorless oil: NMR (CDCl$_3$) δ=0.06 (6H, s), 0.90 (9H, s), 1.07 (3H, d, J=7 Hz), 1.35 (3H, s), 4.25 (1H, m), 4.8-5.2 (2H, m), 5.32 (1H, m), 5.50 (1H, m), 5.76 (1H, d of d, J=10 Hz, 5 Hz), 6.00 (1H, d, J=10 Hz).

(c)

6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-(tert-butyldimethylsilyloxy)-2-hydroxy-3,4,5,6-tetrahydro-2H-pyran (3c)

A mixture of the compound (3b) (0.259 g, 0.42 mmol), toluenesulfonic acid pyridinium salt (70 mg), tetrahydrofuran (6 ml), acetic acid (2 ml) and water (2 ml) was stirred at ambient temperature for 60 hours. The reaction mixture was poured into cold water and extracted with diethyl ether. The combined extracts washed with water and 5 percent aqueous sodium bicarbonate, and dried over magnesium sulfate then concentrated in vacuo. The residue was purified by preparative thin layer chromatography over silica gel eluted with methylene chloride:acetone (100:1) to give the desired product: NMR (CDCl$_3$) $\delta$ =0.05 and 0.13 (3H, 2s), 0.90 and 0.94 (9H, 2s), 1.07 (3H, d, J=7 Hz), 1.36 (3H, s), 5.80 (1H, d of d, J=10 Hz, 5 Hz), 6.00 (1H, d, J=10 Hz).

(d)

6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (3d)

To a stirred solution of pyridine (0.218 g, 2.76 mmol) in methylene chloride (6.5 ml) at ambient temperature under nitrogen was added solid chromium oxide (0.138 g, 1.38 mmol). The mixture was stirred for 30 minutes and then a solution of the compound (3c) (0.11 g, 0.21 mmol) in methylene chloride (2.5 ml was added quickly. The reaction mixture was stirred at ambient temperature for 30 minutes and then filtered through silica gel. The silica gel was washed with methylene chloride. The combined filtrate and washings were diluted with diethyl ether and washed successively with dilute hydrochloric acid, and 5 percent aqueous sodium bicarbonate, dried over magnesium sulfate and concentrated in vacuo. The residue was purified by preparative thin layer chromatography over silica gel eluted with methylene chloride:acetone (100:1) to give the desired product: NMR (CDCl$_3$) $\delta$ =0.08 6H, s), 0.87 (9H, s), 1.08 (3H, d, J=7 Hz), 1.37 (3H, s), 2.60 (2H, d, J=4.5 Hz), 4.27 (1H, m), 4.60 (1H, m), 5.31 (1H, m), 5.50 (1H, m), 5.74 (1H, d of d, J=10 Hz, 5 Hz), 6.00 (1H, d, J=10 Hz).

(e)

6(R)-[2-[8(S)-(1-Methylcyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one To a stirred solution of the compound (3d) (46 mg, 0.087 mmol) and acetic acid (46 μl0.8 mmol) in tetrahydrofuran (2 ml) was add n-tetrabutylammonium fluoride (0.5 ml, 1M in tetrahydrofuran, 0.5 mmol). The reaction mixture was stirred for 20 hours at ambient temperature. The reaction mixture was then poured into cold water and extracted with diethyl ether. The combined extracts were washed with 5 percent sodium bicarbonate, dried over magnesium sulfate and concentrated in vacuo. The residue was purified by preparative thin layer chromatography to afford the desired product, after trituration with diethyl ether/hexane, as a solid, mp 157-9° C.

Anal. Calcd for C$_{25}$H$_{36}$O$_5$: C, 71.60; H, 9.03. Found: C, 71.21; H, 8.92.

NMR (CDCl$_3$) $\delta$ =0.91 (3H, d, J=7 Hz), 1.10 (3H, d, J=7 Hz), 1.39 (3H, s), 2.63 (1H, s, m of d, J=17 Hz), 2.78 (1H, d of d, J=17 Hz, 5 Hz), 4.40 (1H, m), 4.65 (1H, m), 5.40 (1H, m), 5.55 (1H, m), 5.80 (1H, d of d, J=17 Hz, 5 Hz), 6.02 (1H, d, J=10 Hz).

EXAMPLE 4

Preparation of 6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a)

6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)-(tertbutyldimethylsilyloxy)-2-(2-tetrahydropyranyloxy)-3,4,5,6-tetrahydro-2H-pyran (4a)

Utilizinq the general procedure of Example 3(b)but employing methyl disulfide (90 μl, 1 mmol) in place of methyliodide, the compound (3a) (0.23g, 0.38 mmol) was converted into desired product as a yellow oil: NMR (CDCl$_3$) $\delta$ =0.07 (6H, s), 0.88 (9H, s), 1.12 (3H, d, J=7 Hz), 2.02 (3H, s), 4.24 (1H, m), 4.85-5.25 (2H, m), 5.37 (1H, m), 5.50 (1H, m), 5.75 (1H, d of d, J=10 Hz, 5 Hz), 5.96 (1H, d, J=10 Hz).

(b)

6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)-(tertbutyldimethylsilyloxy)-2-hydroxy-3,4,5,6-tetrahydro-2H-pyran (4b)

Utilizing the general procedure of Example 3(c) the compound (4a) was converted into the desired product as a pale yellow oil: NMR (CDCl$_3$) $\delta$ =0.05 and 0.11 (3H, 2s), 0.86 and 0.91 (9H, 2s), 1.10 (3H, d, J=7 Hz), 2.02 (3H, s), 5.74 (1H, d of d, J=10 Hz, 5 Hz), 5.96 (1H, d, J=10 Hz).

(c)

6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)-(tertbutyldimethylsilyloxy)-3,4,5,6-tetrahydro-2H-pyran-2-one (4c)

To a stirred mixture of the compound (4b) (0.163 g, 0289 mmol) in toluene (8 ml) was added freshly prepared silver carbonate/celite (0.7 g). The reaction mixture was heated under nitrogen on a steam bath for 25 minutes. The solid was filtered off and the filtrate concentrated in vacuo. The residue was dissolved in toluene (8 ml) treated with silver carbonate/celite and heated on a steam bath for 25 minutes. This cycle was repeated for a total of seven times. The final residue was purified by preparative thin layer chromatography on silica gel eluted with methylene chloride:acetone (100:1) to give the desired product as a colorless oil: NMR (CDCl$_3$) $\delta$ =0.08 (3H, s), 0.91 (9H, s), 1.11 (3H, d, J=7 Hz), 2.03 (3H, s), 2.55 (2H, d, J=4 Hz), 4.27 (1H, m), 4.57 (1H, m), 5.35 (1H, m), 5.48 (1H, m), 5.74 (1H, d of d, J=10 Hz, 5 Hz), 5.97 (1H, d, J=10 Hz).

(d)

6(R)-[2-[8(S)-(1-Methylthiocyclobutanecarbonyloxy)-2(S),6(R)-dimethyl-1,2,6,7,8,8a(R)-hexahydronaphthyl-1(S)]ethyl]-4(R)hydroxy-3,4,5,6-tetrahydro-2H-pyran-2-one Utilizing the general procedure of Example 3(e), the compound (4c) (90 mg, 0.16 mmol) was converted into the desired product as an off-white solid. mp 134–6° C.

Anal. Calcd for $C_{25}H_{36}O_5S$: C, 66.93; H, 8.09.
Found: C, 66.79; H, 8.30.

NMR (CDCl$_3$) δ = 0.38 (3H, d, J = 7 Hz), 1.12 (3H, d, J = 7 Hz), 2.05 (3H, s), 4.36 (1H, m), 4.62 (1H, m), 5.3–5.6 (2H, m), 5.75 (1H, d of d, J = 10 Hz, 5 Hz), 5.97 (1H, d, J = 10 Hz).

EXAMPLE 5

Preparation of 6(R)-[2-[8(S)-[1-(3-Hydroxypropyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 1-(tert-Butyldiphenylsilyloxy)propyl iodide (5a)

To a stirred mixture of 3-iodo-1-propanol (4.3 g, 23 mmol) and imidazole (3.74 g, 55 mmol) in dimethylformamide (20 ml) was added tert-butylchlorodiphenylsilane (6.8 g, 24.7 mmol) at ambient temperature and the reaction mixture was stirred for 20 hours. The reaction mixture was then poured into cold water. The combined extracts were washed with dilute hydrochloric acid, 5 percent sodium bicarbonate dried over magnesium sulfate, and concentrated in vacuo. The residue was purified by flash chromatography over silica gel eluted with CH$_2$Cl$_2$:hexane (1:5, v:v) and further by distillation to afford the desired product as a colorless oil: b.p. 134–5° C./0.01 mmHg.

(b)

6(R)-[2-[8(S)-[1-(3-tert-Butyldiphenylsilyloxy)propylcyclobutanecarbonyloxy]-2(S),6(R)dimethyl-1,2,6,7,8,8a(R)-hexahydronaphthyl-1(S)]ethyl]-4(R)-(tert-butyldimethylsilyloxy)2-(2-tetrahydropyrenyl)-3,4,5,6-tetrahydro-2H-pyran (5b)

Utilizing the general procedure of Example 3(b) but employing the compound (5a) (0.596 g, 1.4 mmol) in place of methyliodide, the compound (3a) (0.555 g 0.92 mmol) was converted into the desired product as a colorless viscous oil: NMR (CDCl$_3$) δ = 0.86 (9H, s), 1.04 9H, s), 4.20 (1H, m), 4.8–5.2 (2H, m), 5.25–5.55 (2H, m), 5.72 (1H, d of d, J = 10 Hz, 5 Hz), 5.95 (1H, d, J = 10 Hz), 7.25–7.5 (6H, m), 7.5–7.75 (4H, m).

(c)

6(R)-[2-[8(S)-[1-(3-tert-Butyldiphenylsilyloxy)propylcyclobutanecarbonyloxy]-2(S),6(R)dimethyl-1,2,6,7,8,8a(R)-hexahydronaphthyl-1(S)]ethyl]-4(R)-(tert-butyldimethylsilyloxy)-2-hydroxy-3,4,5,6-tetrahydro-2H-pyran (5c)

Utilizing the general procedure of Example 3(c), the compound (5b) (0.553 g, 0.61 mmol) was converted into the desired product as a viscous oil: NMR (CDCl$_3$) δ = 0.87 and 0.92 (9H, 2s), 1.05 (9H, s), 3.62 (2H, t, J = 6 Hz), 5.75 (1H, d of d, J = 10 Hz, 5 Hz), 6.00 (1H, d, J = 10 Hz), 7.3–7.5 (6H, m), 7.6–7.8 (4H, m).

(d)

6(R)-[2-[8(S)-[1-(3-tert-Butyldiphenylsilyloxy)propylcyclobutanecarbonyloxy]-2(S),6(R)dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-One (5d)

Utilizing the general procedure of Example 3(d), the compound (5c) (0.192 g, 0.235 mmol) was converted into the desired product as a viscous oil: NMR (CDCl$_3$) δ = 0.05 (6H, s), 0.88 (9H, s), 1.04 (9H, s), 2.53 (2H, d, J = 4 Hz), 3.60 (2H, t, J = 6 Hz), 4.23 (1H, m), 4.57 (1H, m), 5.3~5.6 (2H, m), 5.72 (1H, dd, J = 10 Hz, 5 Hz), 5.96 (1H, d, J = 10 Hz), 7.3~7.5 (6H, m), 7.5~7.7 (4H, m).

(e)

6(R)-[2-[8(S)-[1-(3-Hydroxypropyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Utilizing the general procedure of Example 3(e), the compound (5d) (0.103 g, 0.126 mmol) was converted into the desired product as a glassy oil.

Anal. Calcd for $C_{25}H_{40}O_6 \cdot 0.25H_2O$: C, 69.72; H, 8.78.
Found: C, 69.59, H, 8.91. NMR (CDCl$_3$) δ = 0.90 (3H, d, J = 7 Hz), 1.13 (3H, d, J = 7 Hz), 2.62 (1H, m of d, J = 18 Hz), 2.74 (1H, d of d, J = 18 Hz, 4 Hz), 3.5~3.7 (2H, m), 4.30 (1H, m), 4.64 (1H, m), 5.40 (1H, m), 5.58 (1H, m), 5.79 (1H, d of d, J = 10 Hz, 5 Hz) 6.01 (1H, d, J = 10 Hz).

EXAMPLE 6

Preparation of 6(R)-[2-[8(S)-(1-Hydroxymethyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) Ethyl 1-benzyloxymethylcyclobutanecarboxylate (6a)

n-Butyl lithium solution (2.20 M in hexane, 23.2 ml, 51 mmol) was added via a syringe under nitrogen to a stirred solution of di-i-propylamine (5.13 g, 51 mmol) and HMPA (3.5 ml, 20 mmol) in THF (100 ml) at 0° C. The resulting mixture was stirred at 0° C. for 10 minutes, cooled to −78° C., added a solution of ethyl cyclobutanecarboxylate (5 g, 39 mmol) in THF (10 ml) via a dropping funnel. The resulting mixture was stirred at −78° C. for 0.5 hour, then warmed to 0° C. and stirred for 0.5 hour. The mixture was recooled to −78° C., treated with a solution of benzyl chloromethyl ether (6.58 g, 42 mmol) in THF (10 ml). The resulting mixture was stirred at −78° C. for 20 minutes, slowly warmed to room temperature and stirred for 1 hour. It was poured into cold water, extracted with diethyl ether. The ethereal extract was washed successively with diluted HCl, 5% NaHCO$_3$, dried, filtered and evaporated to give a residue. This residue was purified by distillation to afford the desired product as a pale yellow oil: bp 102–3° C. (0.02 mm); NMR (CDCl$_3$) δ = 1.23 (3H, t, J = 7 Hz), 1.6~2.6 (6H, m), 3.68 (2H, s), 4.15 (2H, q, J = 7 Hz), 4.53 (2H, s), 7.30 (5H, s).

(b) Ethyl 1-hydroxymethylcyclobutanecarboxylate (6b)

A mixture of ethyl 1-benzyloxymethylcyclobutanecarboxylate (6.57 g, 26.5 mmol), 10% palladium on carbon (0.4 g) and ethanol (100 ml) was hydrogenated on a Parr Shaker for 4 hours. The catalyst was removed by filtration. The filtrate was evaporated in vacuo to leave the desired product as a colorless oil: NMR (CDCl$_3$) δ=1.26 (3H, t, J=7 Hz), 1.8~2.6 (6H, m), 2.61 (H, s), 3.78 (2H, s), 4.15 (2H, q, J=7 Hz).

(c) 1-Acetoxymethylcyclobutanecarboxylic Acid (6c)

Sodium hydroxide pellets (1.48 g, 37 mmol) was added to a stirred mixture of ethyl 1-hydroxymethylcyclobutanecarboxylate (4.14 g, 26.1 mmol), water (4 ml) and 95% ethanol (20 ml). The resulting mixture was stirred at room temperature overnight, then concentrated on a rotary evaporator. The residue was treated with toluene (100 ml). Evaporation of this mixture gave a flaky residue which was further dried under high vacuum. The final residue was treated with pyridine (25 ml) and acetic anhydride (15 ml). The resulting mixture was stirred at room temperature for 18 hours, then heated on a steam bath for 20 minutes. It was cooled to room temperature, added crushed ice, then slowly treated with concentrated HCl (12N, 30 ml) with vigorous stirring. It was extracted with a mixture of diethyl ether (120 ml) and methylene chloride (40 ml). The extract was washed with water (4×100 ml), dried, filtered and evaporated to yield the desired product as a yellow oil: NMR (CDCl$_3$) δ=1.82-2.7 (9H, m containing a singlet at 2.076δ), 4.40 (2H, s), 11.46 (H, bs).

(d) 1-Acetoxymethylcyclobutanecarbonyl chloride (6d)

Thionyl chloride (1.65 ml, 22.7 mmol) was added to neat 1-acetoxymethylcyclobutanecarboxylic acid (3.3 g, 18.9 mmol). The resulting mixture was stirred at room temperature for 1 hour, then heated on a steam bath for 5 minutes. After cooling, the excess thionyl chloride, HCl and SO$_2$ were removed under reduced pressure (water aspirator). The remained residue was purified by distillation to provide the desired product as a colorless oil: bp 51-3° C. (0.02 mm); NMR (CDCl$_3$) δ=1.8~2.7 (9H, m containing a singlet at 2.04 δ), 4.40 (2H, s).

(e)
6(R)-[2-[8(S)-(1-Acetoxymethyl)cyclobutanecarbonyloxy]-2(S),6(R)-dimethyl-1,2,6,7,8,8a(R)-hexahydronaphthyl-1(S)]ethyl]-4(R)-(tertbutyldimethylsilyloxy)-3,4,5,6-tetrahydro-2H-pyran-2-one (6e)

By following the general procedure described in Example 1(a) but using compound 6(d) in place of 1-methylcyclopropanecarbonyl chloride, there was obtained the desired 6(e) as a pale yellow oil: NMR (CDCl$_3$) δ=0.08 (6H, s), 0.89 (9H, s), 1.05 (3H, d, J=7 Hz), 1.98 (3H,s), 2.57 (2H, d, J=4 Hz), 4.30 (2H, s), 4.31 (H, m), 4.62 (H, m), 5.47 (2H, m), 5.73 (H, d of d, J=10.5 Hz), 6.00 (H, d, J=10 Hz).

(f)
6(R)[2-[8(S)-(1-Acetoxymethyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6,-tetrahydro-2H-pyran-2-one (6f)

Utilizing the general procedure of Example 1(b), the compound 6(e) was converted to the desired product as a yellow oil: NMR (CDCl$_3$) δ=0.90 (3H, d, J=7 Hz), 1.06 (3H, d, J=7 Hz), 2.00 (3H, s), 2.72 (2H, d, J=4 Hz), 3.35 (H, bs), 4.30 (2H, s), 4.40 (H, m), 4.70 (H, m), 5.3~5.6 (2H, m), 5.78 (H, d of d, J=10, 5 Hz), 6.00 (H, d, J=10 Hz).

(g)
6(R)-[2-[8(S)-(1-Hydroxymethyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Sodium hydroxide (1N, 2.5 ml, 25 mmol) was added to a stirred mixture of compound 6(f) (0.432 g, 0.91 mmol) in methanol (10 ml) and acetonitrile (1 ml). The resulting mixture was stirred at 0° C. for 10 minutes, then warmed to room temperature and stirred for 2 hours. The reaction mixture was diluted with water, acidified with HCl (2N, 2.5 ml) and extracted with methylene chloride twice. The combined extracts were dried, filtered and evaporated to leave a residue which was dissolved in benzene (15 ml), heated at reflux for 1.5 hours. After the evaporation, the solid residue was purified by flash chromatography on a silica gel column. Elution of the column with methylene chloride:acetone:i-propanol=20:2:1 (v:v:v) gave the desired product as a white solid which was recrystallized from methylene chloride-hexane: mp 162-5° C.; NMR (CDCl$_3$) δ=0.91 (3H, d, J=7 Hz), 1.12 (3H, d, J=7 Hz), 3.75~3.95 (2H, m), 4.39 (H, m), 4.65 (H, m), 5.48 (H, m), 5.58 (H, m), 5.81 (H, d of d, J=10, 5 Hz), 6.04 (H, d, J=10 Hz). Anal Calcd for C$_{25}$H$_{36}$O$_6$: C, 69.42; H, 8.39.

Found: C, 69.51; H, 8.44.

EXAMPLE 7

Preparation of
6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one By following the general procedures described in Example 3(a) to (e), and using cyclopentanecarbonyl chloride to replace cyclobutanecarbonyl chloride, the above titled compound was prepared.

(a)
6(R)-[2-[8(S)-(Cyclopentanecarbonyloxy)-2(S),6(R)-dimethyl-1,2,6,7,8,8a(R)-hexahydronaphthyl-1(S)]ethyl]-4(R)-(tert-butyldimethylsilyloxy)-2-(2-tetrahydropyranyloxy)-3,4,5,6-tetrahydro-2H-pyran (7a)

NMR (CDCl$_3$) δ=0.05 (6H, s), 0.90 (9H, d), 1.09 (3H, d, J=9 Hz), 4.25 (1H, m) 4.8~b 5.2 (2H, m), 5.31 (1H, m), 5.53 (1H, m), 5.77 (1H, d of d, J=10, 5 Hz), 6.00 (1H, d, J=10 Hz).

(b)
6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-(tert-butyldimethylsilyloxy)-2-(2-tetrahydyropyranyloxy)-3,4,5,6-tetrahydro-2H-pyran (7b)

NMR (CDCl$_3$) δ=0.06 (6H, s), 0.90 (9H, s), 1.10 (3H, d, J=7 Hz), 1.24 (3H, s) 4.25 (1H, m), 4.8~5.2 (2H, m), 5.30 (1H, m), 5.50 (1H, m), 5.75 (1H, d of d, J=10, 5 Hz), 5.99 (1H, d, J=10 Hz).

(c)
6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-(tert-butyldimethylsilyloxy)-2-hydroxy-3,4,5,6-tetrahydro-2H-pyran (7e)

NMR (CDCl$_3$) δ=0.90 and 0.94 (9H, two s), 1.08 (3H, d, J=7 Hz), 1.20 (3H, s), 5.74 (1H, d of d, J=10, 5

Hz), 5.97 (1H, d, J=10 Hz). (d) 6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-(tert-butyldimethylsilyloxy)-3,4,5,6,-tetrahydro-2H-pyran 2-one (7d) NMR (CDCl$_3$) δ=0.07 (6H, s), 0.88 (9H, s), 1.07 (3H, d, J=7 Hz), 1.20 (3H, s), 2.55 (2H, d, J=4 Hz), 4.27 (1H, m), 4.57 (1H, m), 5.30 (1H, m), 5.50 (1H, m), 5.75 (1H, d of d, J=10, 5 Hz), 6.00 (1H, d, J=10 Hz).

(e)
6(R)-[2-[8(S)-(1-Methylcyclopentanecarbonyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one m.p. 148~51° C.; NMR (CDCl$_3$) δ=0.89 (3H, d, J=7 Hz), 1.07 (3H, d, J=7 Hz) 1.21 (3H, s), 4.35 (1H, m), 4.68 (1H, m), 5.35 (1H, m), 5.50 (1H, m), 5.75 (1H, d of d, J=10, 5 Hz), 6.00 (1H, d, J=10 Hz).

EXAMPLE 8

Preparation of
6(R)-[2-[8(S)-(1-Methylthiocyclopentanecarbonyloxy)-2(S),6(R)-dimethyl-1,2,6,7,8,8a(R)hexahydronaphthyl-1(S)]ethyl]-4(R)-hydroxy-3,4,5,6-tetrahydro-2H-pyran-2-one By following the general procedures described in Example 4 and using compound 7(a) instead of compound 3 (b), the above-title compound was prepared.

(a)
6(R)-[2-[8(S)-(1-Methylthiocyclopentanecarbonyloxy)-2(S),6(R)-dimethyl-1,2,6,7,8,8a-(R)-hexahydronaphthyl-1(S)]ethyl]-4(R)-(tertbutyldimethylsilyloxy)-2-(2-tetrahydropyranyloxy)-3,4,5,6,-tetrahydro-2H-pyran (8a)

NMR (CDCl$_3$) δ=0.05 6H, s), 0.90 (9H, s), 1.13 (3H, d, J=7 Hz), 2.08 (3H, s), 4.27 (1H, m), 4.9~5.3 (2H, m), 5.3~5.7 (2H, m), 5.85 (1H, d of d, J=10, 5 Hz), 6.05 (1H, d, J=10 Hz).

(b)
6(R)-[2-[8(S)-(1-Methylthiocyclopentanecarbonyloxy)-2(S),6(R)-dimethyl-1,2,6,7,8,8a-(R)-hexahydronaphthyl-1(S)]ethyl]-4(R)-(tert-butyldimethylsilyloxy)-2-hydroxy-3,4,5,6-tetrahydro-2H-pyran (8b)

NMR (CDCl$_3$) δ=0.04 and 0.13 (6H, two s), 0.90 and 0.94 (9H, two s), 1.14 (3H, d, J=7 Hz), 2.10 (3H, s), 5.79 (1H, d of d, J=10, 5 Hz), 6.03 (1H, d, J=10 Hz).

(c)
6(R)-[2-[8(S)-(1-Methylthiocyclopentanecarbonyloxy)-2(S),6(R)-dimethyl-1,2,6,7,8,8a(R)-hexahydronaphthyl-1(S)]ethyl]-4(R)-(tertbutyldimethylsilyloxy)-3,4,5,6-tetrahydro-2H-pyran-2-one (8c)

NMR (CDCl$_3$) δ=0.11 (6H, s), 0.89 (9H, s), 1.10 (3H, d, J=7 Hz), 2.07 (3H, s) 2.55 (2H, d, J=4 Hz), 4.24 (1H, m), 4.53 (1H, m), 5.24 (1H, m), 5.45 (1H, m), 5.72 (1H, d of d, J=10, 5 Hz), 5.95 (1H, d, J=10 Hz).

(d)
6(R)-[2-[8(S)-(1-Methylthiocyclopentanecarbonyloxy)-2(S),6(R)-dimethyl-1,2,6,7,8,8a-(R)-hexahydronaphthyl-1(S)]ethyl]-4(R)-hydroxy 3,4,5,6-tetrahydro-2H-pyran-2-one NMR (CDCl$_3$) δ=0.90 (3H, d, J=7 Hz), 1.11 (3H, d J=7 Hz), 2.10 (3H, s), 2.62 (1H, m of d, J=17 Hz), 2.76 (1H, d of d, J=17, 5 Hz) 4.38 (1H, m), 4.62 (1H, m), 5.38 (1H, m), 5.53 (1H, m), 5.78 (1H, d of d, J=10, 5 Hz), 5.98 (1H, d, J=10 Hz): ms (M+1)$^+$=463.

EXAMPLE 9

Preparation of
6(R)-[2-[8(S)-[(1-Phenylmethyl)cyclobutanecarbonyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) Ethyl 1-Phenylmethylcyclobutanecarboxylate (9a)

Utilizing the general procedure described in Example 6(a) but using benzyl chloride in place of benzyl chloromethyl ether, there was obtained the desired product as a pale yellow oil: bp 88–91° C. 0.5 mm); NMR (CDCl$_3$) δ=1.15 (3H, t, J=7 Hz), 1.6~2.6 (6H, m), 3.10 2H, s), 4.10 (2H, q, J=7 Hz), 7.20 (5H, bs).

(b) 1-Phenylmethylcyclobutanecarboxylic Acid (9b)

A mixture of ethyl 1-phenylmethylcyclobutanecarboxylate (4.16 g, 19.1 mmol), sodium hydroxide (1.2 g, 30 mmol) in ethanol (95%, 20 ml and water (5 ml) was stirred at room temperature for 60 hours. The reaction mixture was poured into cold water and extracted with diethyl ether. The aqueous Phase was separated, acidified with HCl (2N, 35 ml) and extracted with diethyl ether. The latter extract was washed with water, dried, filtered and evaporated to afford the desired product as a pale yellow oil: NMR (CDCl$_3$) δ=1.7~2.6 (6H, m), 3.10 (2H, s), 7.22 (5H, s).

(c) 1-Phenylmethylcyclobutanecarbonyl Chloride (9c)

Utilizing the general procedure described in Example 6(d), compound 9(b) was converted to the desired product as a colorless oil: bp 78–81° C. (0.01 mm); NMR (CDCl$_3$) δ=1.7~2.7 (6H, m), 3.20 (2H, s), 7.23 (5H, m).

(d)
6(R)-[2-[8(S)-[(1-Phenylmethyl)cyclobutanecarbonyloxy]-2(S),6(R)-dimethyl-1,2,6,7,8,8a-(R)-hexahydronaphthyl-1(S)]ethyl]-4(R)-(tertbutyldimethylsilyloxy)-3,4,5,6-tetrahydro-2H-pyran-2-One (9d)

Utilizing the general procedure described in Example 1(a) but using compound 9(c) in place of 1-methylcyclopropanecarbonyl chloride, there was obtained the desired product as a yellow oil: NMR (CDCl$_3$) δ=0.07 (6H, s), 0.89 (9H, s), 2.55 (2H, d, J=4 Hz), 2.95 (H, d, J=15 Hz), 3.15 (H, d, J=15 Hz), 4.27 (H, m), 4.53 (H, m), 5.45 (2H, m), 5.72 (H, d of d, J=10, 5 Hz), 5.98 (H, d, J=10 Hz), 7.17 (5H, bs).

(e)
6(R)-[2-[8(S)-[(1-Phenylmethyl)cyclobutanecarbonyloxy]-2(S),6(R)-dimethyl-1,2,6,7,8,8a-(R)-hexahydronaphthyl-1(S)]ethyl]-4(R)-hydroxy-3,4,5,6-tetrahydro-2H-pyran-2-one Utilizing the general procedure described in Example 1(b), compound 9(d) was converted to the desired product as a glassy gum: NMR (CDCl$_3$) δ=0.86 (3H, d, J=7 Hz), 0.87 (3H, d, J=7 Hz), 2.61 (H, m of d, J=16 Hz), 2.74 (H, d of d, J=16, 7 Hz), 3.04 (H, d, J15 Hz), 3.15 (H, d, J=15 Hz), 4.34 (H, m), 4.54 (H, m), 5.48 (2H, m), 5.77 (H, d of d, J=10, 5 Hz), 5.99 (H, d, J=10 Hz), 7.14~7.28 (5H, m).

Anal. Calcd for $C_{31}H_{40}O_5 \cdot 0.5H_2O$: C, 74.22; H, 8.24. Found: C, 74.12; H, 8.14.

EXAMPLE 10

Preparation of 6(R)-[2-[8(S)-[1-[(4-hydroxyphenyl)methyl]cyclobutanecarbonyloxy]-2(S),6(R)-dimethyl-1,2,6,7,8,8a(R)-hexahydronaphthyl-1(S)ethyl]-4-(R)-hydroxy-3,4,5,6-tetrahydro-2H-pyran-2-one By following the same procedures described in Example 6, steps (a)–(g), but using 4-benzyloxybenzyl chloride in place of benzyl chloromethyl ether in the first step, there were obtained successively:

(a) Ethyl 1-(4-Benzyloxyphenyl)methylcyclobutanecarboxylate (10a)

NMR (CDCl₃) δ1.20 (3H, t, J=7 Hz), 1.7~2.5 (6H, m), 3.0 (2H, s), 4.08 (2H, q, J=7 Hz), 5.0 (2H, s), 6.82 (2H, d, J=8 Hz), 7.03 (2H, d, J=8 Hz), 7.36 (5H, m).

(b) Ethyl 1-(4-Hydroxyphenyl)methylcyclobutanecarboxylate (10b)

NMR (CDCl₃) δ=1.20 (3H, t, J=7 Hz), 1.6~2.6 (6H, m), 3.0 (2H, s), 4.12 (2H, q, J=7 Hz), 6.68 (2H, d, J=8 Hz), 6.95 (2H, d, J=8 Hz).

(c) 1-(4-Acetoxyphenyl)methylcyclobutanecarboxylic Acid (10c)

NMR (CDCl₃) δ=1.7~2.7 (6H, m), 2.31 (3H, s), 3.10 (2H, s), 6.95 (2H, d, J=8 Hz), 7.13 (2H, d, J=8 Hz), 10.96 (H, bs).

(d) 1-(4-Acetoxyphenyl)methylcyclobutanecarbonyl chloride

NMR (CDCl₃) δ=1.7~2.7 (6H, m), 2.24 (3H, s), 3.18 (2H, s), 7.05 (2H, d, J=8 Hz), 7.22 (2H, d, J=8 Hz).

(e) 6(R)-[2-[8(S)-[1-(4-Acetoxyphenyl)methylcyclobutanecarbonyloxy]-2(S),6(R)-dimethyl-1,2,6,7,8,8a(R)-hexahydronaphthyl-1(S)ethyl]-4(R)-(tert-butyldimethylsilyloxy)-3,4,5,6-tetrahydro-2H-pyran-2-one (10e)

NMR (CDCl₃) δ=0.1 (6H, s), 0.89 (9H, s), 2.36 (3H, s), 2.57 (2H, d, J=4 Hz), 2.95 (H, d, J=14 Hz), 3.17 (H, d, J=14 Hz), 4.30 (H, m), 4.60 (H, m), 5.50 (2H, m), 5.74 (H, d of d, J=10, 5 Hz), 6.00 (H, d, J=10 Hz), 6.95 (2H, d, J=8 Hz), 7.17 (2H, d, J=8 Hz).

(f) 6(R)-[2-[8(S)-[1-(4-Acetoxyphenyl)methylcyclobutanecarbonyloxy]-2(S),6(R)-dimethyl-1,2,6,7,8,8a(R)-hexahydronaphthyl-1(S)ethyl]-4(R)-hydroxy-3,4,5,6-tetrahydro-2H-pyran-2-one (10f)

NMR (CDCl₃) δ=0.87 (3H, d, J=7 Hz), 0.91 (3H, d, J=7 Hz), 2.26 (3H,s), 2.98 (H, d, J=14 Hz), 3.18 (H, d, J=14 Hz), 4.28 (H, m), 4.50 (H, m), 5.46 (2H, m), 5.77 (H, d of d, J=10, 5 Hz), 6.01 (H, d, J=10 Hz), 6.99 (2H, d, J=8 Hz), 7.17 (2H, d, J=8 Hz).

(g) 6(R)-[2-[8(S)-[1-[(4-Hydroxyphenyl)methyl]cyclobutanecarbonyloxy]-2(S),6(R)-dimethyl-1,2,6,7,8,8a(R)-hexahydronaphthyl-1(S)ethyl]-4(R)-hydroxy-3,4,5,6-tetrahydro-2H-pyran-2-one (10g)

NMR (CDCl₃) δ=0.82 (3H, d, J=7 Hz), 1.04 (3H, d, J=7 Hz), 2.63 (H, m of d, J=17 Hz), 2.78 (H, d of d, J=17, 5 Hz), 3.03 (H, d, J=15 Hz), 3.16 (H, d, J=15 Hz), 4.40 (2H, m), 5.31 (H, m), 5.49 (H, m), 5.75 (H, d of d, J=10, 5 Hz), 5.98 (H, d, J=10 Hz), 6.72 (2H, d, J=8 Hz), 7.03 (2H, d, J=8 Hz).

Anal. Calcd for $C_{31}H_{40}O_6$: C, 73.20; H, 7.93.

Found C, 72.94; H, 8.27.

EXAMPLE 11-16

Utilizing the general procedures from Example 1 to 4 the following compounds are prepared from the appropriate starting materials:

| Compound | |
|---|---|
| 11 | 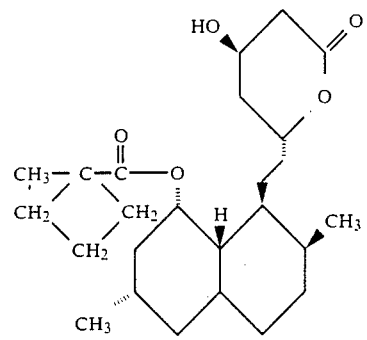 |
| 12 | 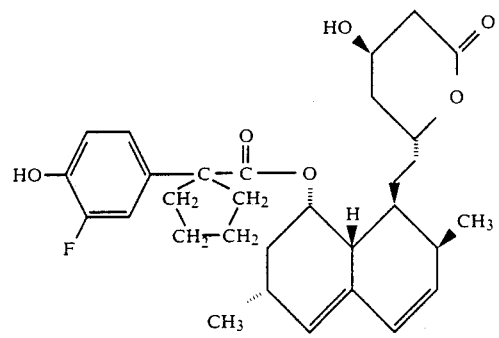 |
| 13 | 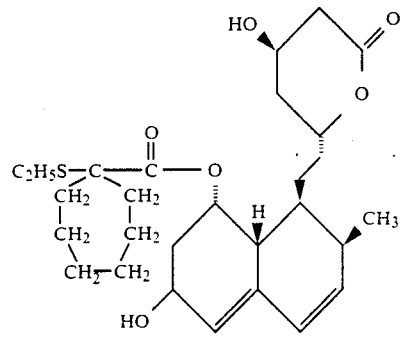 |

| Compound | |
|---|---|
| 14 | 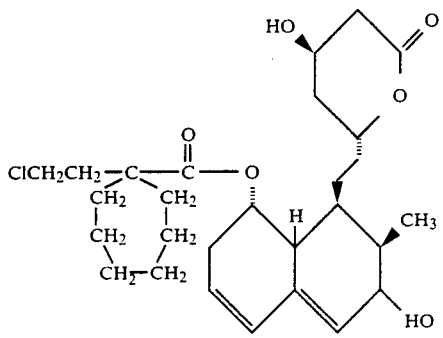 |
| 15 | 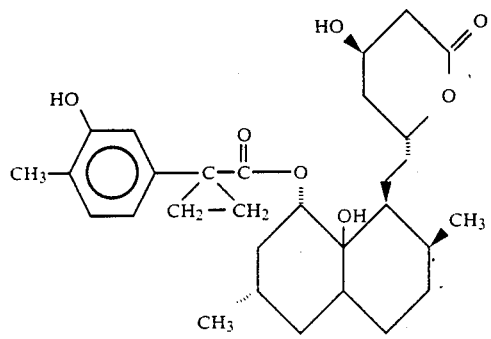 |

EXAMPLE 16

Preparation of Alkali and Alkaline Earth Salts of Compound II

To a solution of 42 mg of the lactone from Example 1 in 2 ml of ethanol is added 1 ml of aqueous NaOH (1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 17

Preparation of Methyl Ester of Compound II

To a solution of 400 mg of the lactone from Example 1 in 100 ml of absolute methanol is added 10 ml 0.1 M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amyl alcohol, isoamyl alcohol, 2-dimethylaminoethanol, benzyl alcohol, phenethanol, 2-acetamidoethanol, and the like, the corresponding esters are obtained.

EXAMPLE 18

Preparation of free Hydroxy Acids

The sodium salt of the compound II from Example 16 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 19

As a specific embodiment of a composition of this invention, 20 mg of the lactone from Example 1 is formulated with sufficient finely divided lactose to provide a total amount of 580 to 590 mg to fill a size 0 hard gelatin capsule.

What is claimed is:

1. A compound represented by the following general structural formula (II):

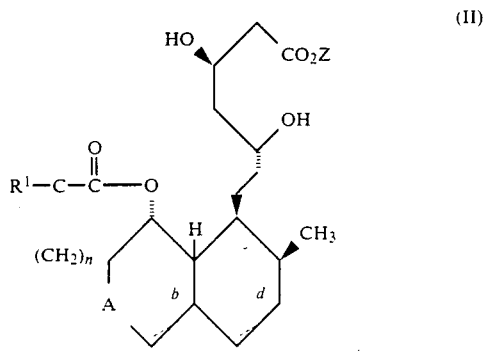

(II)

wherein:

n is 2 to 7;

$R^1$ is $C_{1-6}$alkyl substituted with a group selected from halogen or hydroxy; $C_{1-6}$alkylthio; phenylmethyl or 4-hydroxyphenylmethyl;

A is

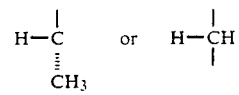

b and d represent single bonds, or both b and d represent double bonds;

Z is hydrogen, $C_{1-5}$alkyl or $C_{1-5}$alkyl substituted with a group selected from phenyl, dimethylamino or acetylamino; and pharmaceutically acceptable salts of the compounds of the formula (II) in which Z is hydrogen.

2. A compound of claim 1 wherein
n is 2 to 5; and
$R^1$ is $C_{1-6}$alkyl; hydroxy-$C_{1-6}$alkyl; $C_{1-6}$alkylthio; phenylmethyl; or 4-hydroxyphenylmethyl.

3. A compound of claim 2 wherein n is 2.
4. A compound of claim 2 wherein n is 3.
5. A compound of claim 2 wherein n is 4.
6. A compound of claim 2 wherein n is 5.

7. A hypocholesterolemic, hypolipidemic pharmaceutical composition comprising a nontoxic therapeutically effective amount of a compound of claim 1 and a pharmaceutically acceptable carrier.

8. A composition according to claim 7 wherein:
n is 2 to 5; and
$R^1$ is $C_{1-6}$ alkyl; hydroxy-$C_{1-6}$ alkyl; $C_{1-6}$ alkylthio; phenyl; or hydroxyphenyl.

9. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

10. A method of inhibiting cholesterol biosynthesis comprising the administration to a subject in need of such treatment a nontoxic therapeutically effective amount of a compound of claim 1.

11. A method of claim 10 wherein:
n is 2 to 5; and
$R^1$ is $C_{1-6}$ alkyl hydroxy-$C_{1-6}$ alkyl; $C_{1-6}$ alkylthio; phenyl; or hydroxyphenyl.

12. A compound of claim 3 which is 7-[1,2,6,7,8, 8a(R)-hexahydro-2(S), 6(R)-dimethyl-8(S)-(1-methylcyclopropanecarbonyloxy)-1(S)-naphthyl]-3(R), 5(R)-dihydroxyheptanoic acid.

13. A compound of claim 4, which is 7-[1,2,6,7,8, 8a(R)-hexahydro-2(S), 6(R)-dimethyl-8(S)-(1-methylcyclobutanecarbonyloxy)-1(S)-naphthyl]-3(R), 5(R)-dihydroxyheptanoic acid.

14. A compound of claim 4 which is 7-[1,2,6,7,8, 8a(R)-hexahydro-2(S), 6(R)-dimethyl-8(S)-(1-methylthiocyclobutanecarbonyloxy)-1(S)-naphthyl]-3(R),5(R)-dihydroxyheptanoic acid.

15. A compound of claim 4 which is 7-[1,2,6,7,8, 8a(R)-hexahydro-2(S),6(R)-dimethyl-8(S)-[1-(3-hydroxypropyl)cyclobutanecarbonyloxy]-1(S)-naphthyl]-3(R),5(R)-dihydroxyheptanoic acid.

16. A compound of claim 4 which is 7-[1,2,6,7,8,8a(R)-hexahydro-2(S),6(R)-dimethyl-8(S)-[1-[(4-hydroxyphenyl) methyl]cyclobutanecarbonyloxy)-1(S)-naphthyl]-3(R),5(R)-dihydroxyheptanoic acid.

17. A compound of claim 4 which is 7-[1,2,6,7,8, 8a(R)-hexahydro-2(S),6(R)-dimethyl-8(S)-[1-(hydroxymethyl)cyclobutanecarbonyloxy]-1(S)-naphthyl]-3(R),5(R)-dihydroxyheptanoic acid.

18. A compound of claim 4 which is 7-[1,2,6,7,8, 8a(R)-hexahydro-2(S),6(R)-dimethyl-8(S)-8 1-(1-phenylmethyl) cyclobutanecarbonyloxy]-1(S)-naphthyl]-3(R),5(R)-dihydroxyheptanoic acid.

19. A compound of claim 5 which is 7-[1,2,6,7,8, 8a(R)-hexahydro-2(S),6(R)-dimethyl-8(S)-(1-methylcyclopentanecarbonyloxy)-1(S)-naphthyl]-3(R),5(R)-dihydroxyheptanoic acid.

20. A compound of claim 5 which is 7-[1,2,6,7,8, 8a(R)-hexahydro-2(S),6(R)-dimethyl-8(S)-(1-methylthiocycopentanecarbonyl)-1(S)-naphthyl]-3(R),5(R)-dihydroxyheptanoic acid.

21. A compound of claim 6 which is 7-[1,2,6,7,8, 8a(R)-hexahydro-2(S),6(R)-dimethyl-8(S)-(1-methylcyclohexanecarbonyloxy)-1(S)-naphthyl]-3(R),5(R)-dihydroxyheptanoic acid.

22. A composition according to claim 8 wherein the therapeutically active ingredient is selected from the group consisting of
(1) 7-[1,2,6,7,8,8a(R)-hexahydro-2(S),6(R)-dimethyl-8(S)-(1-methylcyclopropanecarbonyloxy)-1(S)-naphthyl]-3(R),5(R)-dihydroxyheptanoic acid;
(2) 7-[1,2,6,7,8,8a(R)-hexahydro-2(S),6(R)-dimethyl-8(S)-(1-methylcyclobutanecarbonyloxy)-1(S)-naphthyl]-3(R),5(R)-dihydroxyheptanoic acid;
(3) 7-[1,2,6,7,8,8a(R)-hexahydro-2(S),6(R)-dimethyl-8(S)-(1-methylthiocyclobutanecarbonyloxy)-1(S)naphthyl]-3(R),5(R)-dihydroxyheptanoic acid;
(4) 7-[1,2,6,7,8,8a(R)-hexahydro-2(S),6(R)-dimethyl-8(S)-(1-(3-hydroxypropyl)cyclobutanecarbonyloxy]1(S)-naphthyl]-3(R),5(R)-dihydroxyheptanoic acid;
(5) 7-[1,2,6,7,8,8a(R)-hexahydro-2(S),6(R)-dimethyl-8(S)-[1-[(4-hydroxyphenyl)methyl]-cyclobutanecarbonyloxy]-3(R),5(R)-dihydroxyheptanoic acid;
(6) 7-[1,2,6,7,8,8a(R)-hexahydro-2(S),6(R)-dimethyl-8(S)-[(1-hydroxymethyl)cyclobutanecarbonyloxy]-3(R),5(R)-dihydroxyheptanoic acid;
(7) 7-[1,2,6,7,8,8a(R)-hexahydro-2(S),6(R)-dimethyl-8(S)-[1-(1-phenylmethyl)cyclobutanecarbonyloxy]-3(R),5(R)-dihydroxyheptanoic acid;
(8) 7-[1,2,6,7,8,8a(R)-hexahydro-2(S),6(R)-dimethyl-8 (S)-(1-methylcyclopentanecarbonyloxy]-3(R),5(R)-dihydroxyheptanoic acid;
(9) 7-[1,2,6,7,8,8a(R)-hexahydro-2(S),6(R)-dimethyl-8(S)-(1-methylthiocyclopentanecarbonyl)-3(R),5(R)-dihydroxyheptanoic acid;
(10) 7-[1,2,6,7,8,8a(R)-hexahydro-2(S),6(R)-dimethyl-8(S)-(1-methylcyclocyclohexanecarbonyloxy)-3(R), 5(R)-dihydroxyheptanoic acid.

23. A method of claim 11 wherein the therapeutically active ingredient is selected from the group consisting of:
(1) 6(R)-[2-[8(S)-[(R)-hexahydro-2(S),6(R)-dimethyl-8(S)-(1-methylcyclopropanecarbonyloxy)-1(S)-naphthyl]-3(R),5(R)-dihydroxyheptanoic acid;
(2) 7-[1,2,6,7,8,8a(R)-hexahydro-2(S),6(R)-dimethyl-8(S)-(1-methylcyclobutanecarbonyloxy)-1(S)-naphthyl]-3(R),5(R)-dihydroxyheptanoic acid;
(3) 7-[1,2,6,7,8,8a(R)-hexahydro-2(S),6(R)-dimethyl-8(S)-(1-methylthiocyclobutanecarbonyloxy)-1(S)-naphthyl]-3(R),5(R)-dihydroxyheptanoic acid;
(4) 7-[1,2,6,7,8,8a(R)-hexahydro-2(S),6(R)-dimethyl-8(S)-(1-(3-hydroxypropyl)cyclobutanecarbonyloxy]-1(S)-naphthyl]-3(R),5(R)-dihydroxyheptanoic acid;
(5) 7-[1,2,6,7,8,8a(R)-hexahydro-2(S),6(R)-dimethyl-8(S)-[1-[(4-hydroxyphenyl)methyl]cyclobutanecarbonyloxy]-3(R),5(R)-dihydroxyheptanoic acid;
(6) 7-[1,2,6,7,8,8a(R)-hexahydro-2(S),6(R)-dimethyl-8(S)-[(1-hydroxymethyl)cyclobutanecarbonyloxy]-3(R),5(R)-dihydroxyheptanoic acid;
(7) 7-[1,2,6,7,8,8a(R)-hexahydro-2(S),6(R)-dimethyl-8(S)-[1-(1-phenylmethyl)cyclobutanecarbonyloxy]-3(R),5(R)-dihydroxyheptanoic acid;
(8) 7-[1,2,6,7,8,8a(R)-hexahydro-2(S),6(R)-dimethyl-8(S)-(1-methylcyclopentanecarbonyloxy]-3(R),5(R)-dihydroxyheptanoic acid;
(9) 7-[1,2,6,7,8,8a(R)-hexahydro-2(S),6(R)-dimethyl-8(S)-(1-methylthiocyclopentanecarbonyl)-3(R),5(R)-dihydroxyheptanoic acid;
(10) 7-[1,2,6,7,8,8a(R)-hexahydro-2(S),6(R)-dimethyl-8(S)-(1-methylcyclocyclohexanecarbonyloxy)-3(R), 5(R)-dihydroxyheptanoic acid.

* * * * *